United States Patent
Cho et al.

(10) Patent No.: US 11,795,224 B2
(45) Date of Patent: Oct. 24, 2023

(54) ANTI-T-CELL NANOBODY AND NUCLEIC ACID ENCODING SEQUENCE THEREOF, AND USES OF THE SAME

(71) Applicant: China Medical University Hospital, Taichung (TW)

(72) Inventors: Der-Yang Cho, Taichung (TW); Shao-Chih Chiu, Taichung (TW); Shi-Wei Huang, Taichung (TW); Chih-Ming Pan, Taichung (TW); Mei-Chih Chen, Taichung (TW); Yu-Chuan Lin, Taichung (TW); Yeh Chen, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 0 days.

(21) Appl. No.: 17/698,567

(22) Filed: Mar. 18, 2022

(65) Prior Publication Data

US 2022/0306742 A1 Sep. 29, 2022

Related U.S. Application Data

(60) Provisional application No. 63/165,191, filed on Mar. 24, 2021.

(51) Int. Cl.
*C07K 16/28* (2006.01)
*G01N 33/68* (2006.01)

(52) U.S. Cl.
CPC ..... *C07K 16/2809* (2013.01); *G01N 33/6872* (2013.01); *C07K 2317/31* (2013.01); *C07K 2317/52* (2013.01); *C07K 2317/569* (2013.01); *C07K 2317/74* (2013.01); *G01N 2333/7051* (2013.01)

(58) Field of Classification Search
None
See application file for complete search history.

(56) References Cited

FOREIGN PATENT DOCUMENTS

| EP | 4063395 A1 * | 9/2022 |
|----|--------------|--------|
| TW | 201922787 A  | 6/2019 |

OTHER PUBLICATIONS

Moradi-Kalbolandi et al. "Evaluation the potential of recombinant anti-CD3 nanobody on immunomodulatory function", Apr. 2019, Elsevier.

* cited by examiner

*Primary Examiner* — Meera Natarajan
*Assistant Examiner* — Cheom-Gil Cheong
(74) *Attorney, Agent, or Firm* — WPAT, P.C

(57) ABSTRACT

The present disclosure provides an anti-T-cell nanobody that specifically binds to CD3 ε. The present disclosure also provides the nucleic acid sequence of the anti-T-cell nanobody, use of the anti-T-cell nanobody for treating cancer, immunoregulation and activating immune cells, and a method for detecting expression levels of CD3 ε.

9 Claims, 11 Drawing Sheets
(3 of 11 Drawing Sheet(s) Filed in Color)
Specification includes a Sequence Listing.

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: CDR1

<400> SEQUENCE: 1

Gly Val Ile Phe Lys Asn Glu Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2

<400> SEQUENCE: 2

Ala Ser Pro Gly Gly Thr Ile Thr
1               5

<210> SEQ ID NO 3
<211> LENGTH: 23
<212> TYPE: PRT
<213> ORGANISM: Artificial Sequence
<220> FEATURE:
<223> OTHER INFORMATION: CDR3

<400> SEQUENCE: 3

Ala Leu Asp Pro Ser Thr Thr Ser Trp Ser Ile Ile Arg His Gly Pro
1               5                   10                  15

Ser Leu Trp Arg Tyr Ser Gly
            20

<210> SEQ ID NO 4
<211> LENGTH: 24
<212> TYPE: DNA
<213> ORGANISM: Artificial Sequence
<220> FEATURE:
<223> OTHER INFORMATION: CDR1

<400> SEQUENCE: 4
ggagtcatct ttaagaacga gtac                                          24

<210> SEQ ID NO 5
<211> LENGTH: 24
<212> TYPE: DNA
<213> ORGANISM: Artificial Sequence
<220> FEATURE:
<223> OTHER INFORMATION: CDR2

<400> SEQUENCE: 5
gcttcgcctg gtggaacgat taca                                          24

<210> SEQ ID NO 6
<211> LENGTH: 69
<212> TYPE: DNA
```

```
<213> ORGANISM: Artificial Sequence
<220> FEATURE:
<223> OTHER INFORMATION: CDR3

<400> SEQUENCE: 6
gcgttggatc cctcgactac gtcatggtct atcatccgcc acggtccatc gctttggcgt      60
tatagcggc                                                              69
```

ANTI-T-CELL NANOBODY AND NUCLEIC ACID ENCODING SEQUENCE THEREOF, AND USES OF THE SAME

CROSS-REFERENCE TO RELATED APPLICATION

This application claims priority of Provisional Application No. 63/165,191, filed on Mar. 24, 2021, the content of which is incorporated herein in its entirety by reference.

BACKGROUND OF THE INVENTION

1. Field of the Invention

The present invention relates to an anti-T-cell nanobody and nucleic acid encoding sequences thereof, and uses of the same.

2. The Prior Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. However, the current tumor treatments still have the problems of ineffectiveness and strong side effects, and even lead to other immune-related disorders.

CD3ε (CD3 epsilon), a transmembrane protein found on T cells, has been found to be associated with tumors and regulation of immune function. Therefore, researchers have been committed to developing CD3ε as target molecules for tumor identification and regulation of immune function and to find out whether these target molecules have the potential to become anticancer drugs or immunoregulatory drugs.

In order to solve the above-mentioned problems, those skilled in the art urgently need to develop a novel and effective medicament for treating cancer, immunoregulation and activating immune cells for the benefit of a large group of people in need thereof.

SUMMARY OF THE INVENTION

A primary objective of the present invention is to provide an anti-T-cell nanobody that specifically binds to a CD3 ε, comprising an amino acid sequence selected from the group consisting of: SEQ ID NO:1, SEQ ID NO:2, SEQ ID NO:3, and any combination thereof.

According to an embodiment of the present invention, the amino acid sequence is an amino acid sequence of a heavy chain variable domain (VHH) of the anti-T-cell nanobody.

According to an embodiment of the present invention, the anti-T-cell nanobody further comprises a fragment crystallizable region (Fc region).

According to an embodiment of the present invention, the anti-T-cell nanobody is conjugated with a second antibody to form a bispecific T-cell engager (BiTE), triple specific T-cell engager (TriTE), bispecific killer cell engager (BiKE), triple specific killer cell engager (TriKE), or any bispecific antibody.

According to an embodiment of the present invention, the anti-T-cell nanobody activates and/or aggregates CD3 ε-positive cells.

Another objective of the present invention is to provide an isolated nucleic acid encoding the above mentioned anti-T-cell nanobody, wherein the isolated nucleic acid comprises a nucleotide sequence selected from the group consisting of: SEQ ID NO:4, SEQ ID NO:5, SEQ ID NO:6, and any combination thereof.

Another objective of the present invention is to provide a pharmaceutical composition, comprising the above mentioned anti-T-cell nanobody and a pharmaceutically acceptable carrier.

Another objective of the present invention is to provide a method for treating cancer, immunoregulation and activating immune cells, comprising administering to a subject in need thereof the above mentioned pharmaceutical composition.

Another objective of the present invention is to provide a method for detecting expression levels of CD3 ε, comprising contacting a biological sample with the above mentioned anti-T-cell nanobody by immunohistochemistry staining.

According to an embodiment of the present invention, the biological sample is blood, urine, sputum, saliva, body fluid, a tumor, an organ, a tissue or a cell.

In summary, the anti-T-cell nanobody of the present invention has the following effect. The anti-T-cell nanobody can promote T cell proliferation and activation by T cell (i.e., peripheral blood mononuclear cell (PBMC)) proliferation and activation assay, enhances CD3 positive T cell proliferation in PBMCs, enhances CD3 positive T cell proliferation in γδ T (GDT) cells, could recognize CD3 ε protein from cellular lysate of human T cells by Western blotting analysis, can be used for flow cytometry analysis to detect CD3 ε expression on cell samples by immunohistochemistry staining (IHC staining) and flow cytometric analysis, effectively binds to CD3 ε/CD3δ heterodimer within the $K_D$ as 0.5056 nM by surface plasmon resonance binding assay (SPR binding assay), and can be used to detect the expression of CD3 ε on cell samples by immunocytochemistry, thereby achieving the effect of treating cancer, immunoregulation and activating immune cells. In particular, compared with the conventional antibodies, which have the disadvantages of low yield and poor effect, the gene must be transfected into cells by a vector to express the antibody function, the anti-T-cell nanobody of the present invention can be prepared in vitro on a large scale, and directly administered to the individual in need for treatment. In addition, the present invention can also achieve the effect of detecting the expression level of CD3 ε.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1A:
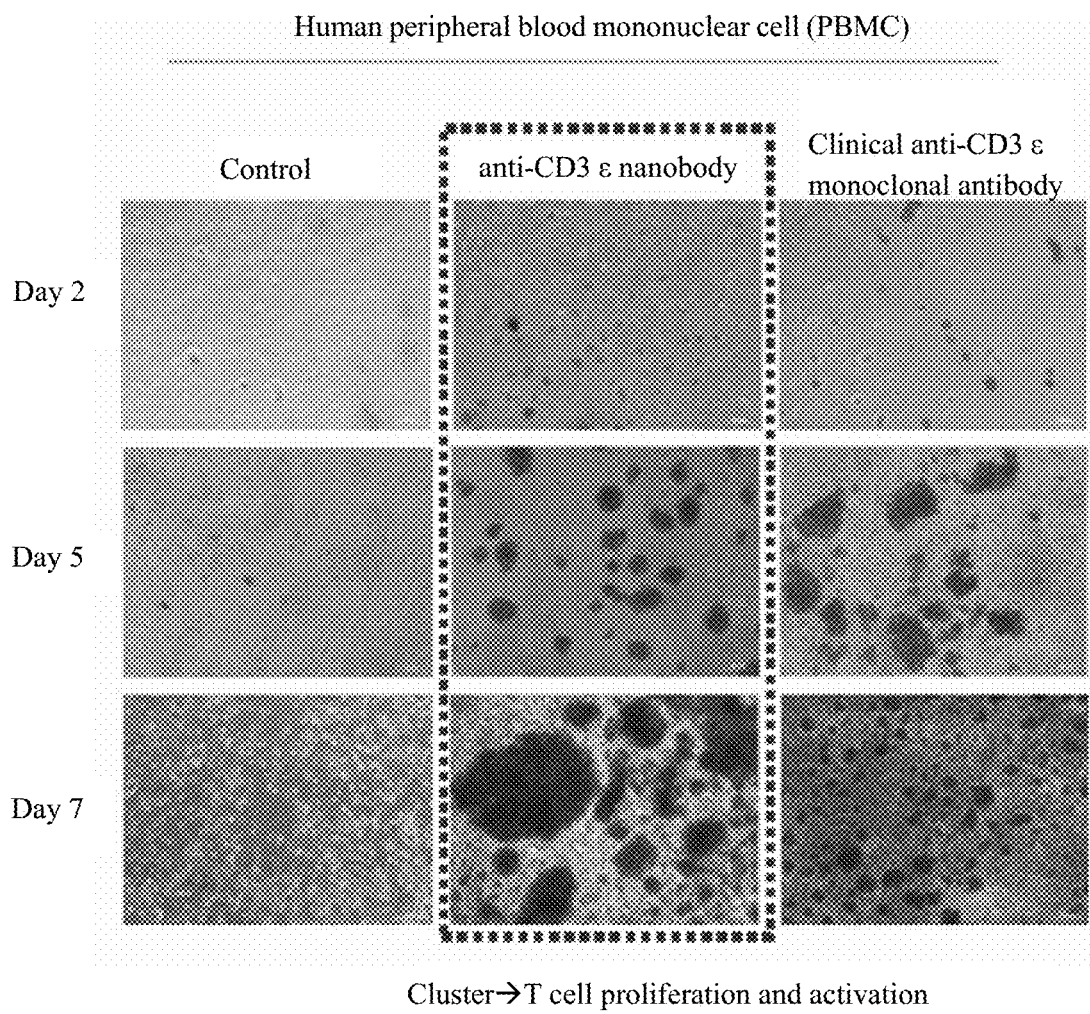
FIGS. 1A and 1B show the result of T cell (i.e., peripheral blood mononuclear cell (PBMC)) proliferation and activation assay of the anti-CD3 ε nanobody.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the term "second antibody" refers to the antibody conjugated with the nanobody to form a bispecific T-cell engager (BiTE), triple specific T-cell engager (TriTE), bispecific killer cell engager (BiKE), triple specific killer cell engager (TriKE), or any bispecific antibody. Preferably, the second antibody includes, but is not limited to, anti-programmed cell death ligand 1 (PD-L1) antibody, anti-programmed cell death ligand 2 (PD-L2) antibody, anti-T-cell immunoglobulin domain and mucin domain 3 (Tim3) antibody, anti-epidermal growth factor receptor (EGFR) antibody, anti-EGFRvIII antibody, anti-human epidermal growth factor receptor 2 (Her2) antibody, anti-B-cell maturation antigen (BCMA) antibody, anti-CD19 antibody, anti-CD20 antibody, anti-CD34 antibody, anti-human leukocyte antigen-G (HLA-G) antibody, anti-epithelial cell adhesion molecule (EpCAM) antibody, anti-mesothelin antibody, anti-New York esophageal squamous cell carcinoma-1 (NY-ESO-1) antibody, anti-glycoprotein 100 (gp100) antibody, and anti-Muc1 antibody.

As used herein, the terms "CD3ε", "CD3 epsilon" and "CD3 ε" can be used interchangeably.

As used herein, the terms "CD3ε nanobody", "CD3ε nb", "CD3ε Nb", "CD3ε nanobody", "anti-CD3 ε nanobody", and "anti-T cell nanobody" can be used interchangeably.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection.

According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid", "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA", "mRNA", "oligonucleotide" and "polynucleotide".

Example 1

Preparation of Anti-CD3 ε Nanobody

In this example, the preparation process of the anti-CD3 ε (CD3 epsilon) nanobody (NB) is as follows. The heavy chain variable domain (VHH) production protocol is as follows. The VHH gene was constructed in expression vector pET22b (Amp resistance) or pSB-init (CmR resistance); The plasmid was identified by restriction enzyme digestion and sequenced verification. 1 μL identified plasmid (about 50 ng) was added to BL21(DE3), and incubated overnight at 37° C. LB culture medium containing resistance was inoculated with a single colony and the cultures were incubated overnight at 37° C., 220 r/min Overnight culture was inoculated in a fresh LB medium (10 L-20 L) containing resistance at a ratio of 1:100, and cultured at 37° C. and 220 r/min. It was cooled to room temperature when the $OD_{600}$ reaches 0.8. Isopropyl-β-D-thiogalactopyranoside (IPTG) was added with a final concentration of 0.1 mM and induced overnight at 20° C., 220 r/min. The cells and supernatant were harvested after cell disruption by centrifugation (20 mM Tris pH8.0, 150 mM NaCl). Supernatant was combined with Ni-NTA beads (1 mL) by flow-through. The Ni-NTA beads were washed and eluted with buffers containing suitable gradient imidazole (10 mM, 20 mM, 50 mM, 100 mM, 250 mM and 500 mM). Elution fraction was analyzed by SDS-PAGE, and the subsequent purification scheme was determined according to the purity and yield of the protein (ion exchange chromatography or gel filtration chromatography). The protein that meets the requirements was separated and purified by gel filtration chromatography, and buffer was replaced with PBS buffer. The protein component was analyzed by SDS-PAGE, the components were merged and concentrated that meet the requirements, filtered with 0.22 μm filter and aliquot. The protein was stored at −20° C. or lower.

The Production and purification of nanobodies are from E. coli. For producing nanobody form E. coli is modified in view of Microb Cell Fact. 2019 Mar. 11; 18(1):47. In brief, the E. coli strain HB2151 was used. The plasmid pET (Creative Biolab) coding an ampicillin resistance was used for cytoplasmic protein production. Freshly transformed E. coli HB2151 with CD3 ε or CD3 ε multyspecific nanobody plasmids would be inoculated in 5 mL of media containing 50 μg/mL of ampicillin and cultivated at 37° C. for overnight. After that, 1 mL of this pre-culture was inoculated into 100 mL medium and grown at 37° C. After overnight cultivation, two EnPresso booster tablets and an additional dose of the glucose releasing enzyme (0.6 U/L) would be added to each 100 mL culture. At the same time, recombinant nanobody protein expression would be induced by the addition of 1 mM IPTG continued as for 24 hours. Then the cultures would be collected and chilled on ice for 5 min and centrifuged for 15 min at 6,000×g and 4° C. After removal of the supernatant, the cell pellets would be purified by high-capacity Myc-tag binding resin using immobilized metal affinity chromatography (IMAC). The gravity-flow-based chromatography would be carried out under native conditions according to the manufacturer protocol (Clontech Laboratories). Efficient cell lysis would be achieved by addition of 1 mL×Tractor cell lysis buffer (Clontech Laboratories) supplemented with EDTA-free protease inhibitor cocktail (Roche Diagnostics) and 25 U endonuclease (Thermo Scientific Pierce) to each 200 mg bacterial cell pellet. After incubation on ice for 15 mM and centrifugation at 10,000×g and 4° C. for 20 mM for removal of cellular debris, the clarified supernatant would be loaded onto a gravity-flow column containing 1 mL of prepacked resin and incubated at room temperature for 30 mM Before elution of the nanobodies by addition of elution buffer containing 300 mM imidazole, the column would be washed twice with increasing imidazole concentrations of 20 and 40 mM. Removal of imidazole and buffer exchange would be achieved by dialysis against PBS using a cellulose ester membrane with a molecular weight cut-off of 3.5-5 kDa (Spectrum Laboratories).

CD3 ε VHHs were generated from HuSdL® Human Single Domain Antibody Library (Creative Biolabs). Briefly, after four rounds of panning with CD3 ε antigen binding/washing/elution, about 100 clones would be picked then the positive monoclonal phage would be selected by phage enzyme linked immunosorbent assay (ELISA). The positive clones would be sequenced by Sanger method to get the nanobody sequences.

The items on the clones for DNA sequencing are shown in Table 1.

TABLE 1

| Item | Clones |
|---|---|
| 1 | 2, 3, 4, 5, 6, 7, 8, 9, 10, 15, 17, 18, 19, 20, 25, 27, 29, 32, 34, 35, 36, 37, 39, 42, 45, 49, 50, 57, 58, 66, 67, 68, 70, 71, 73, 74, 75, 84, 85, 88, 90, 92, 93, 21, 23, 24, 30, 41, 47, 48, 54, 55, 60, 63, 72, 76, 77, 82, 89, 91 |

The clone #2 phagemid was sequenced by Sanger method, then the DNA sequence was thereby translated into corresponding encoded amino acid in silico. The clone #2 phagemid was amplified in E. coli and then supernatant was collected. The amino acid sequences among clone #2 DNA and corresponding CD3ε amino acid, and these nanobody phage clones were all fully-identical. Thereby the clone #2 was picked. The amino acid sequences of anti-CD3 ε nanobody are SEQ ID NO:1, SEQ ID NO:2 and SEQ ID NO:3. The nucleotide sequences encoding the amino acid sequences of anti-CD3 ε nanobody are SEQ ID NO:4, SEQ ID NO:5 and SEQ ID NO:6. Competitive enzyme linked immunosorbent assay (competitive ELISA) was performed on the clone #2, and the procedures are as follows. The clone #2 phagemid was amplified in E. coli and then supernatant was collected. The CD3 ε recombinant protein (0.2 μg) was coated, after washing, 250 μl of clone #2 phage-containing TB medium, mock TB medium and PBS control were added into each well. Next day, the supernatants were discarded, washing with PBST and then incubated with anti-M13 phage horseradish peroxidase (HRP)-conjugated secondary antibody for 2 hours, after washing, TMB (for detection of HRP activity) (50 μl) was added, and the signals were detected by a ELISA reader using 450 nm channel. The result is shown in Table 2.

TABLE 2

| Items | Coating: CD3 ε ($OD_{450}$) |
|---|---|
| Clone#2 | 0.639 |
| Medium | 0.215 |
| phosphate buffered saline (PBS) | 0.221 |
| Secondary antibody is horseradish peroxidase (HRP)-goat anti human IgG (fragment crystallizable region (Fc region)) | |

Example 2

Result of T Cell Proliferation and Activation Assay of Anti-CD3 ε Nanobody

In this example, the procedures of T cell (i.e., peripheral blood mononuclear cell (PBMC)) proliferation and activation assay of the anti-CD3 ε nanobody are as follows. $1 \times 10^6$ of PBMC cells were plating on 12-well plate presence with or without anti-CD3 ε nanobody (1 μg/ml) or clinical CD3 ε monoclonal antibody OKT3 (10 mg/ml, Invitrogen, Cat: MA1-10175). IL-2 50 IU/ml (Gibco, PHC0021) and IL-15 2 μg/ml (Sino Biological, Cat No:10360-H07E) were added. After 5 or 7 days, the total cell numbers were recorded, then stained with FITC-conjugated CD3 monoclonal antibody (OKT3, 11-0037-42, eBioscience) and then analyzed by flow cytometry. The pictures were taken by microscope at 40×. The CD3 positive cells were calculated as % of CD3 cells×total cell number.

Figure 1B:
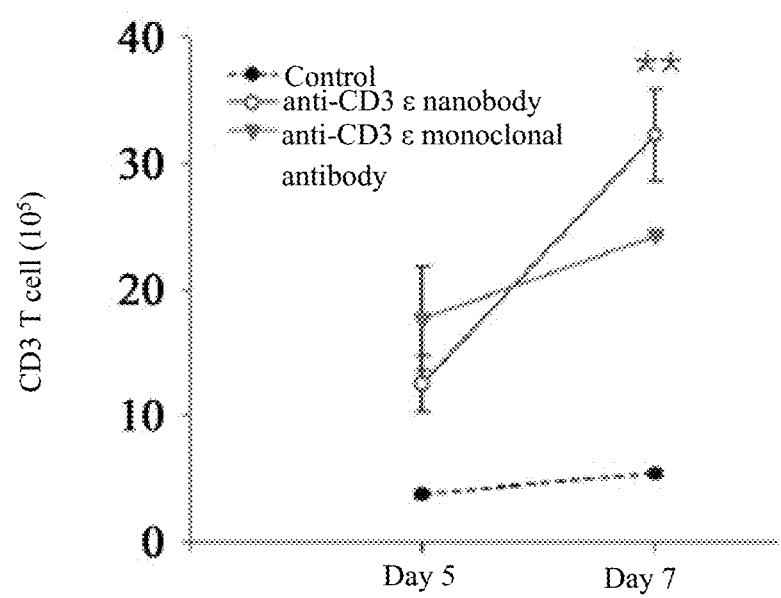

The result of T cell (i.e., PBMC) proliferation and activation assay of the anti-CD3 ε nanobody is shown in FIGS. 1A and 1B. As shown in FIGS. 1A and 1B, the anti-CD3 ε nanobody can promote T cell proliferation and activation.

Example 3

Evaluation of Effect of Anti-CD3 ε Nanobody on Enhancing $CD3^+$ T Cell Proliferation in PBMCs In this example, the procedures regarding evaluation of effect of the anti-CD3 ε nanobody on enhancing $CD3^+$ T cell proliferation in PBMCs are as follows. $1 \times 10^6$ of PBMC cells were plating on 12-well plate presence with or without anti-CD3 ε nanobody (10, 100, 1000, 5000 ng/ml). IL-2 50 IU/ml (Gibco, PHC0021) and IL-15 2 μg/ml (Sino Biological, Cat No:10360-H07E) were added. After 3 or 7 days, the total cell numbers were recorded, then stained with FITC-conjugated CD3 monoclonal antibody (OKT3, 11-0037-42, eBioscience) and then analyzed by flow cytometry. The pictures were taken by microscope at 40×. The CD3 positive cells were calculated as % of CD3 cells×total cell number.

Figure 2A:
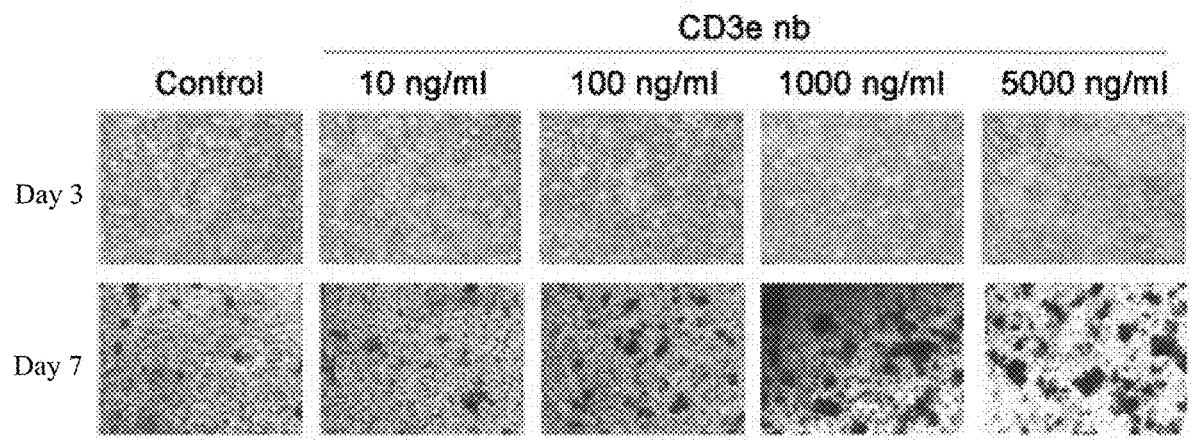
FIGS. 2A to 2C show the result regarding evaluation of effect of the anti-CD3 ε nanobody on enhancing CD3 positive T cell proliferation in PBMCs, wherein CD3ε nb represents anti-CD3 ε nanobody.
Figure 2B:
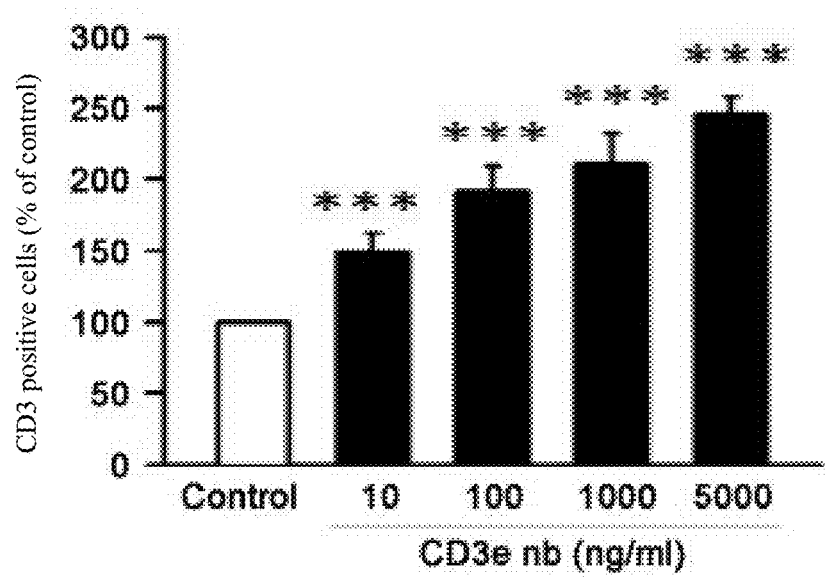
Figure 2C:
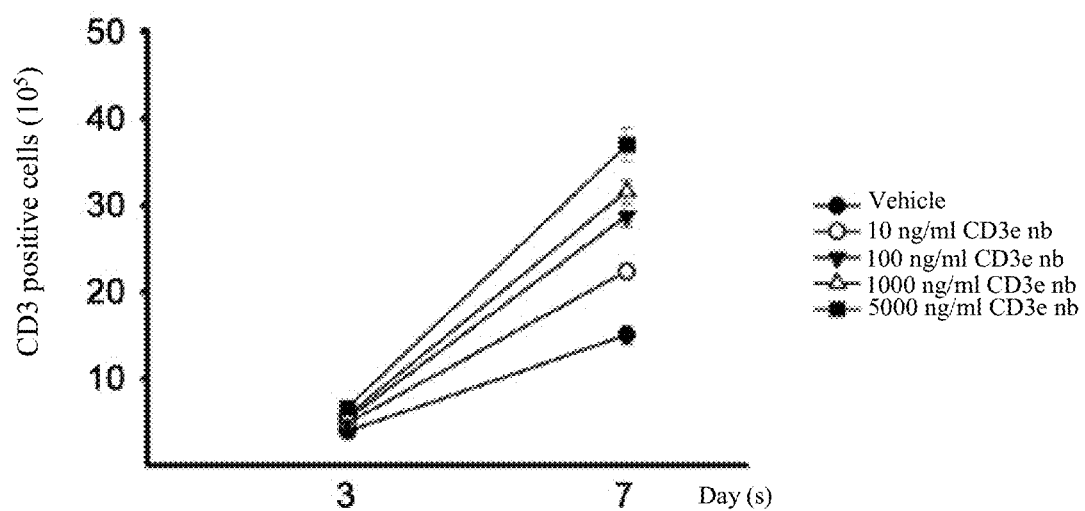
Figure 3A:
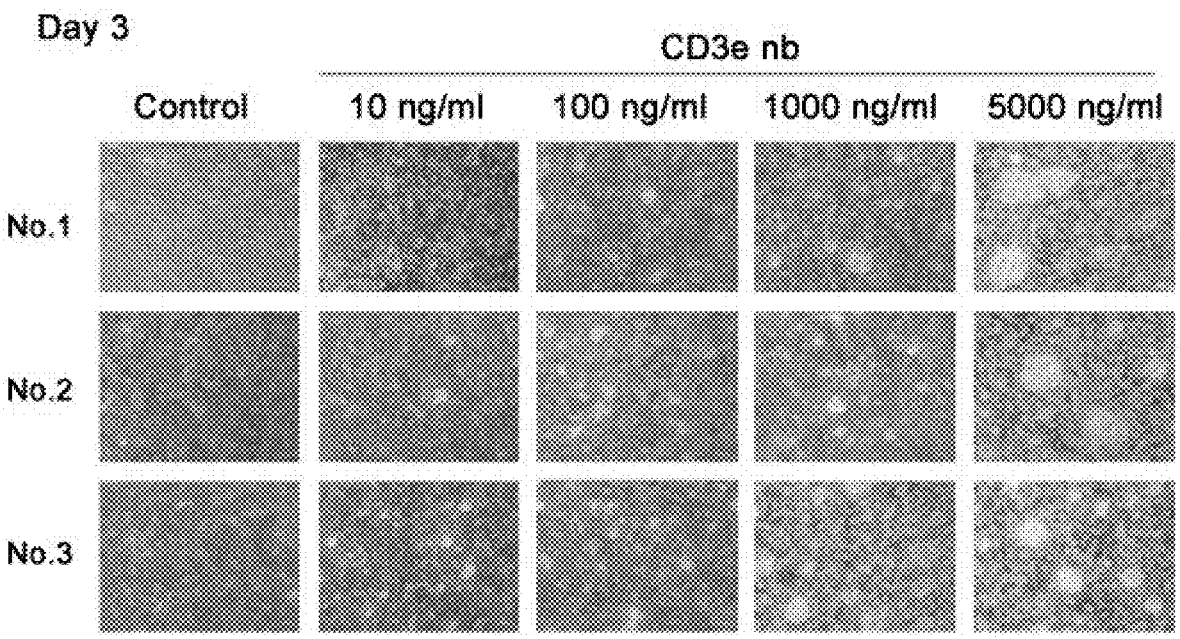
FIGS. 3A to 3D show the result regarding evaluation of effect of the anti-CD3 ε nanobody on enhancing CD3 positive T cell proliferation in γδ T (GDT) cells, wherein CD3ε nb represents anti-CD3 ε nanobody, * represents p<0.05,  represents p<0.01, and * represents p<0.001.
Figure 3B:
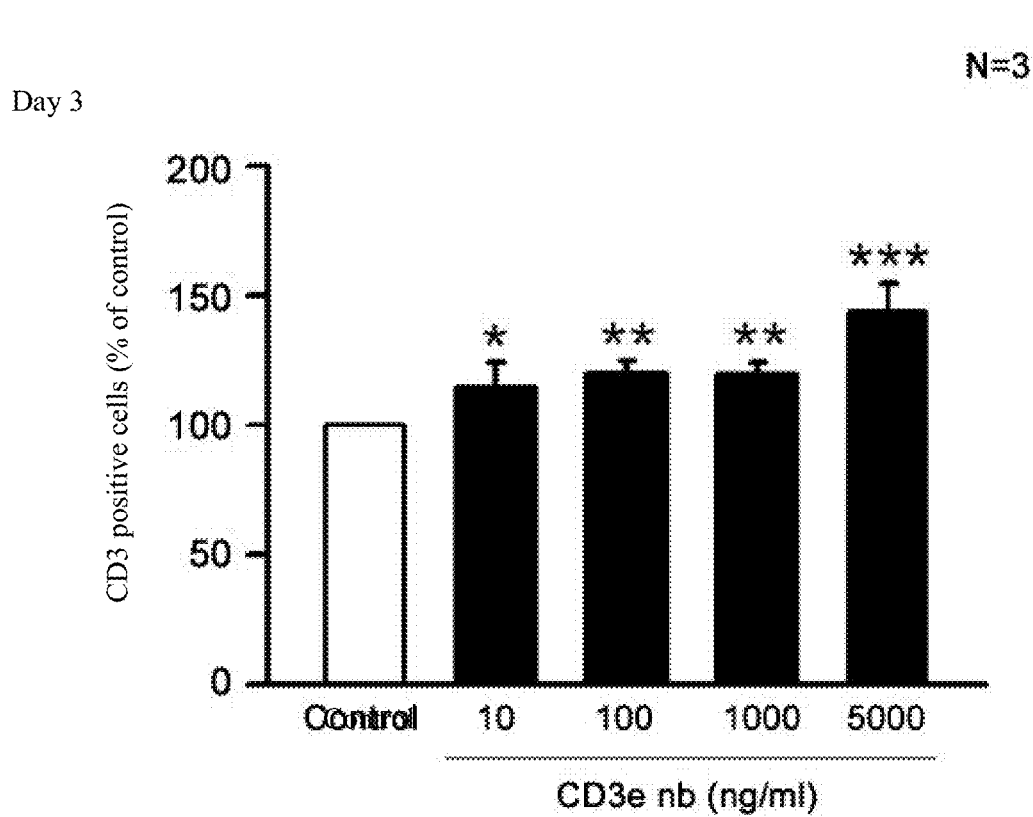
Figure 3C:
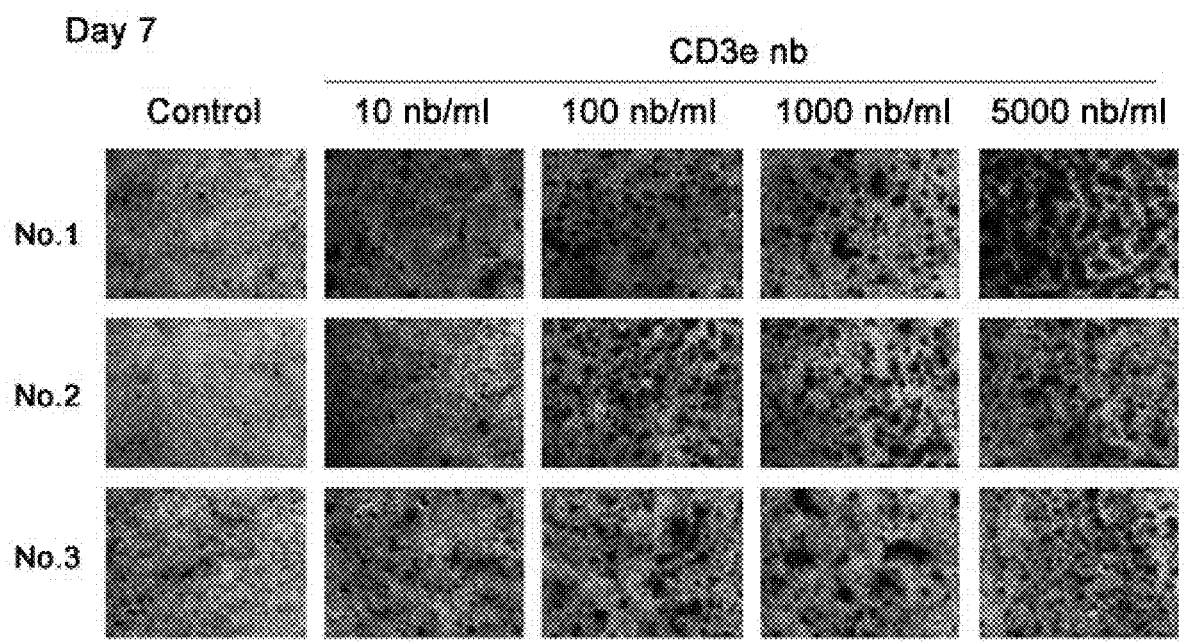
Figure 3D:
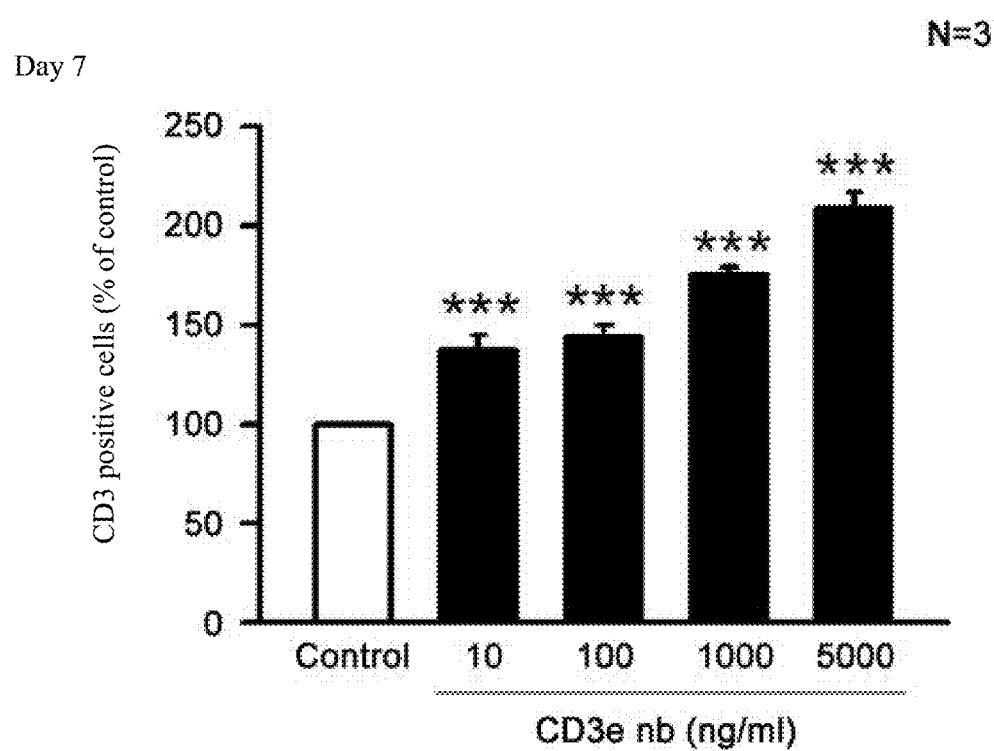

The result regarding evaluation of effect of the anti-CD3 ε nanobody on enhancing CD3 positive T cell proliferation in PBMCs is shown in FIGS. 2A-2C, wherein CD3ε nb represents anti-CD3 ε nanobody. As shown in FIGS. 2A to 2C, the anti-CD3 ε nanobody significantly stimulates $CD3^+$ T cell proliferation with cluster formation in PBMCs.

Example 4

Evaluation of Effect of Anti-CD3 ε Nanobody on Enhancing $CD3^+$ T Cell Proliferation in γδ T (GDT) Cells In this example, the procedures regarding evaluation of effect of the anti-CD3 ε nanobody on enhancing $CD3^+$ T cell proliferation in γδ T (GDT) cells are as follows. $1 \times 10^6$ of primary γδ T (GDT) cells were plating on 12-well plate presence with or without anti-CD3 ε nanobody (10, 100, 1000, 5000 ng/ml). IL-2 50 IU/ml (Gibco, PHC0021) and IL-15 2 μg/ml (Sino Biological, Cat No:10360-H07E) were added. After 3 or 7 days, the total cell numbers were recorded, then stained with FITC-conjugated CD3 monoclonal antibody (OKT3, 11-0037-42, eBioscience) and then analyzed by flow cytometry. The pictures were taken by microscope at 40×. The CD3 positive GDT cells were calculated as % of CD3 GDT cells×total cell number.

The result regarding evaluation of effect of the anti-CD3 ε nanobody on enhancing CD3 positive T cell proliferation in γδ T (GDT) cells is shown in FIGS. 3A-3D, wherein CD3ε nb represents anti-CD3 ε nanobody. The result of this example shows that the anti-CD3 ε nanobody effectively enhances γδ T cell proliferation in a dose dependent manner.

Example 5

Western Blotting Result of Anti-CD3 ε Nanobody

In this example, the procedures of Western blotting for anti-CD3 ε nanobody are as follows. Cells would be harvested in PRO-PREP protein extraction solution (iNtRON, Taipei, Taiwan) containing a protease inhibitor cocktail and vigorously shaken at 4° C. for 15 min, followed by centrifugation. The supernatants would be collected then the protein concentrations were determined by using the Bio-Rad BCA reagent (Bio-Rad Hercules, Calif., USA). A 30 μg of each sample lysate would be subjected to electrophoresis on SDS-polyacrylamide gels then electroblotted onto PVDF membranes. After 5% BSA in TBST blocking, the membranes would be incubated with primary antibodies in TBST at 4° C. overnight. They would be then washed 4 times and incubated with horseradish peroxidase (HRP)-conjugated goat anti-mouse or rabbit IgG (Upstate, Billerica, Mass., USA) for 2 hours. After washing with TBST 4 times, the blots would be incubated for 1 min with the SuperSignal West Pico ECL reagent (Pierce Biotechnology, Rockford, Ill., USA), and chemiluminescence would be detected using by exposure to Kodak-X-Omat film.

Figure 4:
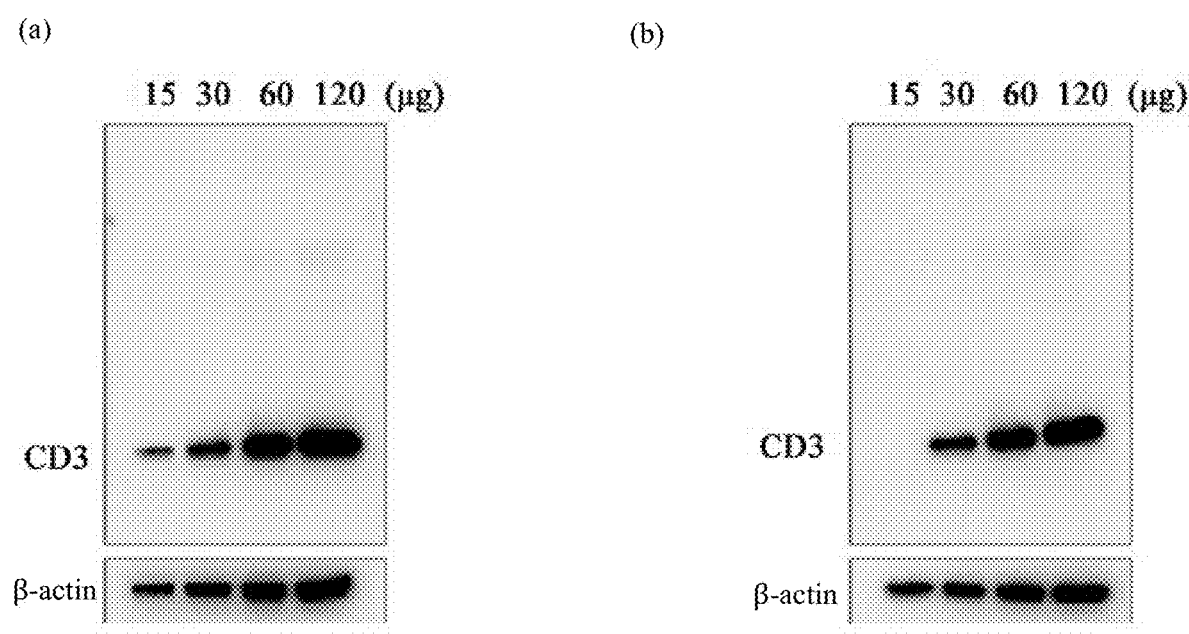
FIG. 4 shows the result of Western blotting analysis of the anti-CD3 ε nanobody, wherein the number in the upper row represents the amount of protein lysate of T cells (μg); (a) the conventional antibody #ab135372 is used, which is an anti-CD3 antibody, the concentration of the primary antibody is 10 μg/ml (1:1000), and the secondary antibody is anti-rabbit-horseradish peroxidase (HRP) (1:1000); (b) the anti-CD3 ε nanobody (i.e., heavy chain variable domain (VHH) nanobody) is used, the concentration of the primary antibody is 1 μg/ml (1:1000), and the secondary antibody is anti-VHH-HRP (1:1000).

The result of Western blotting analysis of the anti-CD3 ε nanobody is shown in FIG. 4, wherein the number in the upper row represents the amount of protein lysate of T cells (μg); (a) the conventional antibody #ab135372 is used, which is an anti-CD3 antibody, the concentration of the primary antibody is 10 μg/ml (1:1000), and the secondary antibody is anti-rabbit-horseradish peroxidase (HRP) (1:1000); (b) the anti-CD3 ε nanobody (i.e., heavy chain variable domain (VHH) nanobody) is used, the concentration of the primary antibody is 1 μg/ml (1:1000), and the secondary antibody is anti-VHH-HRP (1:1000). The result of this example shows that the anti-CD3 ε nanobody could recognize CD3 ε protein from cellular lysate of human T cells by Western blotting analysis.

Example 6

Immunohistochemistry (IHC) Staining Result of Anti-CD3 ε Nanobody

In this example, the procedures of IHC staining of anti-CD3 ε nanobody are as follows. The human PBMC samples would be fixed in 10% formaldehyde and embedded in paraffin. Sections (thickness=3 μm) would be processed with antigen retrieval performed microwaving at 99° C., then the sections would be washed and incubated with $H_2O_2$ for 15 min to block endogenous peroxidases, after then soaking in 5% BSA for 30 min for blocking. The primary antibodies would be incubated overnight at 4° C. After washing, the sections would be then incubated with diluted biotin-conjugated secondary antibodies for 2 h at room temperature or overnight at 4° C. Finally, the sections would be then incubated with polymer for 10 min at room temperature and following diaminobenzidine (DAB, the most sensitive and commonly used chromogenic reactant for horseradish peroxidase) staining, after then the sections would be stained lightly with hematoxylin and eosin and fixed using neutral balata. Quantification of the staining would be performed independently by optical microscope (Nikon) at 40× and 400× magnification.

Figure 5:
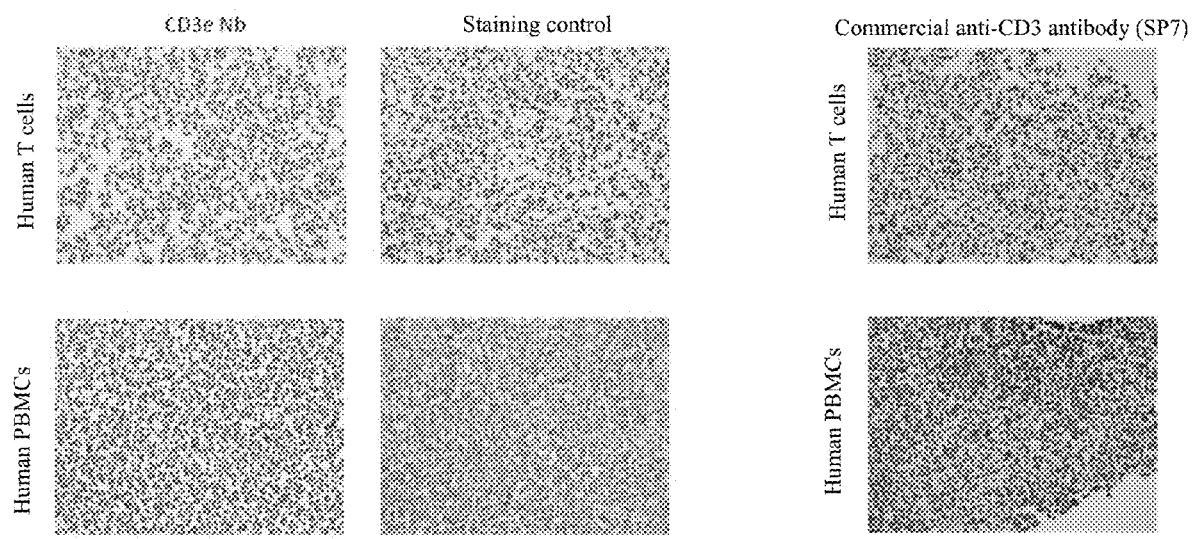
FIG. 5 shows the immunohistochemistry staining (IHC staining) result of the anti-CD3 ε nanobody, wherein CD3ε nb represents anti-CD3 ε nanobody, and SP7 is the conventional anti-CD3 antibody.

The immunohistochemistry staining (IHC staining) result of the anti-CD3 ε nanobody is shown in FIG. 5, wherein CD3ε nb represents anti-CD3 ε nanobody, and SP7 is the conventional anti-CD3 antibody. The result of this example shows that the anti-CD3 ε nanobody can be used for detecting the expression of CD3 ε by IHC staining.

Example 7

Result of Flow Cytometric Analysis of Anti-CD3 ε Nanobody

In this example, the procedures of flow cytometric analysis of the anti-CD3 ε nanobody are as follows. Human PBMCs were staining with FITC-conjugated CD3 ε nanobody (1 µg/ml) and OKT3 antibody (anti-CD3 monoclonal antibody) (10 µg/ml) for 45 min on ice, after washing, the cells were analyzed by flow cytometry using FL1 channel.

Figure 6:
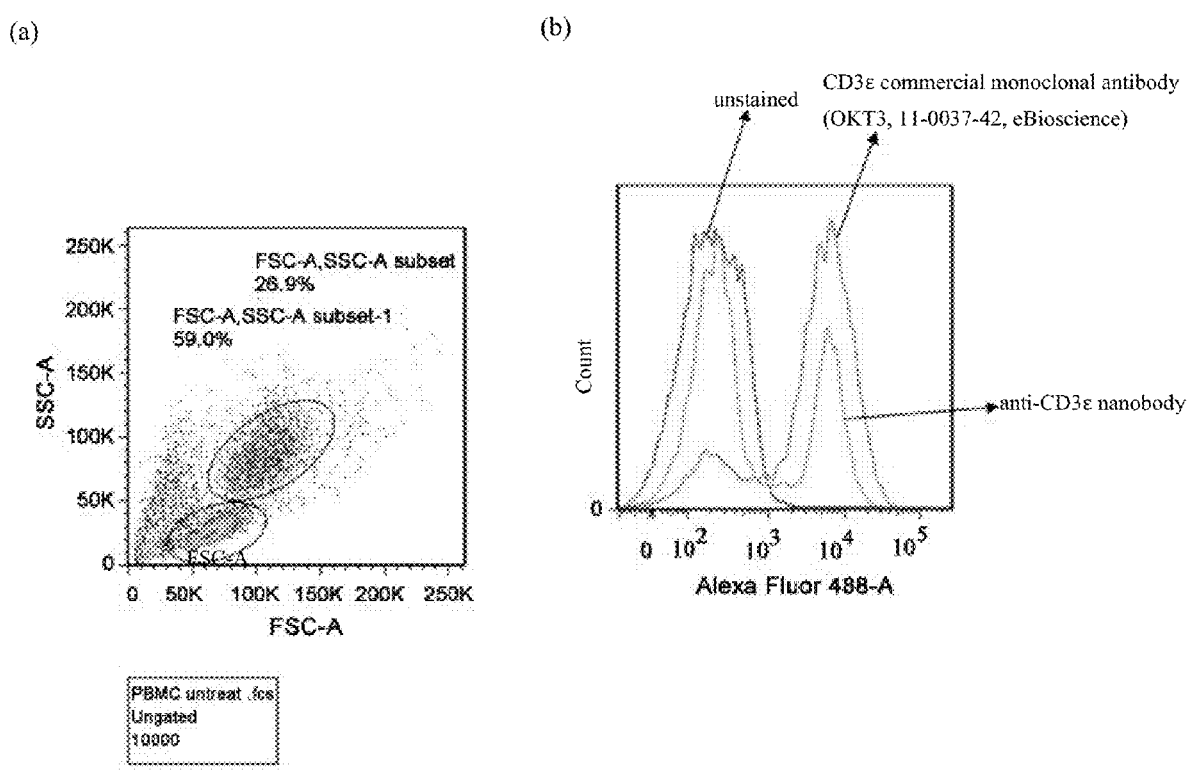
FIG. 6 shows the result of flow cytometric analysis of the anti-CD3 ε nanobody, wherein FSC-A in (a) represents forward scatter area, SSC-A represents side scatter area, fcs represents flow cytometry standard, and Alexa Fluor 488-A in (b) is a bright green fluorescent dye that is excited by laser light at 488 nm.

The result of flow cytometric analysis of the anti-CD3 ε nanobody is shown in FIG. 6, wherein FSC-A in (a) represents forward scatter area, SSC-A represents side scatter area, fcs represents flow cytometry standard, and Alexa Fluor 488-A in (b) is a bright green fluorescent dye that is excited by laser light at 488 nm. As shown in FIG. 6, the anti-CD3 ε nanobody can be used for flow cytometry analysis to detect CD3 ε expression on cell samples.

Example 8

Surface Plasmon Resonance Binding Assay (SPR Binding Assay) Result of Anti-CD3 ε Nanobody to CD3ε/CD3δ Heterodimer In this example, the procedures regarding the surface plasmon resonance binding assay (SPR binding assay) of the anti-CD3 ε nanobody to CD3ε/CD3δ heterodimer are as follows. The CMS or NTA chip, research grade would be performed for SPR analysis by BIAcore T200 (Biacore-GE Healthcare, Piscataway, N.J.). Briefly, protein (CD3ε/CD3δ☐ recombinant protein) sample was diluted in the 10 mM buffer solutions (pH 4.0, 5.5 or 6.0) at the concentration range of 20 µg/mL to give maximum surface retention for immobilization on the chip, following the SURFACE PREPARATION process and choosing the condition of higher surface concentration of ligands (CD3 ε or CD3 ε multispecific nanobodies, 25, 12.5, 6.25, 3.125, 1.5625 and 0.78125 nM) on the chip. Then the regeneration scouting and surface performance test, following REGENERATION SCOUTING and SURPACE PERFORMANCE TEST and then REGENERATION METHOD was selected to run the experiment. And then BINDING ANALYSIS and DIRECT BINDING were selected to investigate protein binding. The KINETIC ANALYSIS would be selected and choose MASS TRANSFER was chosen to run kinetic assay accompany with binding experiment. Data analysis and kinetic constants were determined.

Figure 7:
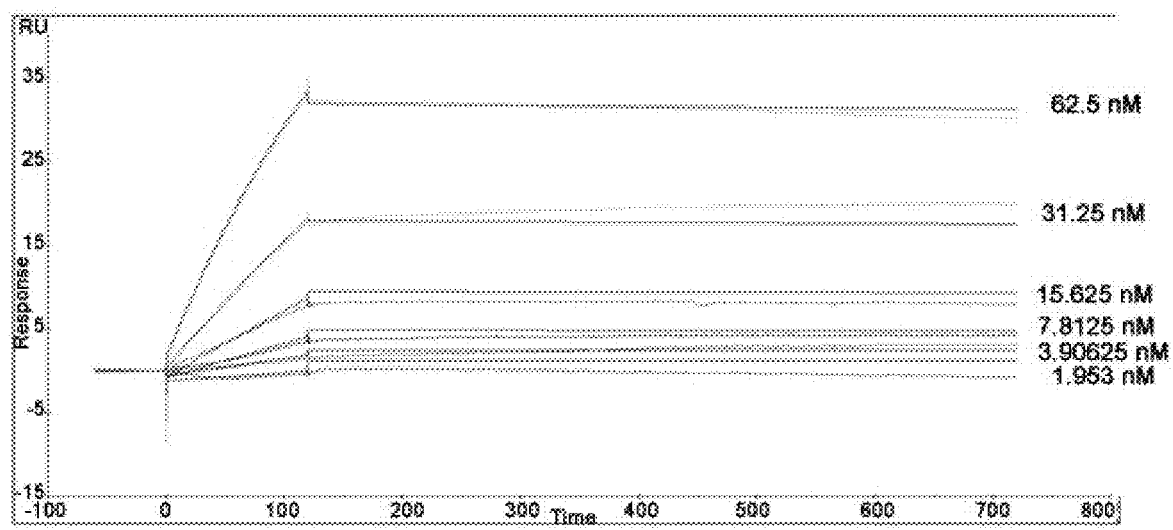
FIG. 7 shows the surface plasmon resonance binding assay (SPR binding assay) result of the anti-CD3 ε nanobody to CD3ε/CD3δ heterodimer, wherein the analyte concentration is 62.5 nM, 31.25 nM, 15.625 nM, 7.8125 nM, 3.90625 nM, and 1.953 nM, the association time is 120 seconds, the dissociation time is 600 seconds, Kd: $5.056 \times 10^{-10}$=0.5056 nM, coated CD3 ε/CD3 δ heterodimer recombination protein (ACROBiosystems, Cat:CDD-H52W1) is used, NTA chip.

The SPR binding assay result of the anti-CD3 ε nanobody to CD3ε/CD3δ heterodimer is shown in FIG. 7, wherein the analyte concentration is 62.5 nM, 31.25 nM, 15.625 nM, 7.8125 nM, 3.90625 nM, and 1.953 nM, the association time is 120 seconds, the dissociation time is 600 seconds, Kd: $5.056 \times 10^{-10}$=0.5056 nM, coated CD3 ε/CD3 δ heterodimer recombination protein (ACROBiosystems, Cat:CDD-H52W1) is used, NTA chip. As shown in FIG. 7, the anti-CD3 ε nanobody effectively binds to CD3ε/CD3δ heterodimer within the $K_D$ as 0.5056 nM.

Example 9

Immunocytochemistry Result of Anti-CD3 ε Nanobody

In this example, the procedures of immunocytochemistry of anti-CD3 ε nanobody are as follows. Cells ($1 \times 10^5$) were seeded on coverslips in a 6-well plate, incubated overnight. After the indicated treatments, cells were fixed in 1% paraformaldehyde, washed with PBS, permeabilized using 0.1% Triton X-100 in PBS containing 0.5% BSA for 30 min, blocked with 2% BSA, and incubated with specific antibodies in 2% BSA/PBS containing 0.05% Tween-20 (PBST). After washing, the cells were incubated with fluorescein-conjugated secondary antibodies, washed with PBST, and mounted using a water-based mounting medium containing an anti-fade agent and 4',6-diamidino-2-phenylindole (DAPI). Images were analyzed under a Leica TCS SP8 X confocal microscope (Leica).

Figure 8:
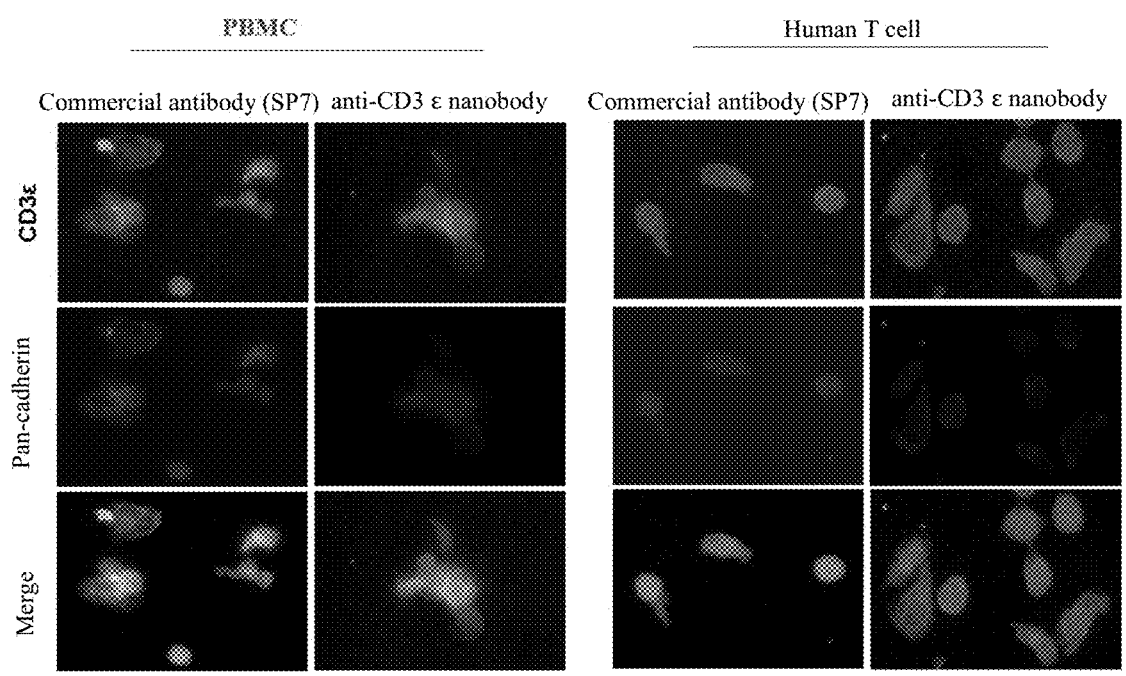
FIG. 8 shows the immunocytochemistry result of the anti-CD3 ε nanobody, wherein the concentration of the anti-CD3 ε nanobody is 1 ng/ml, SP7 is the conventional anti-CD3 antibody (1:500, MA1-90582, Invitrogen), and the secondary antibody is anti-VHH-fluorescein (FITC) (1:5000).

The immunocytochemistry result of the anti-CD3 ε nanobody is shown in FIG. 8, wherein the concentration of the anti-CD3 ε nanobody is 1 ng/ml, SP7 is the conventional anti-CD3 antibody (1:500, MA1-90582, Invitrogen), and the secondary antibody is anti-VHH-fluorescein (FITC)(1:5000). The result of this example shows that the anti-CD3 ε nanobody can be used to detect the expression of CD3 ε on cell samples by immunocytochemistry.

In one example, the anti-T-cell nanobody (i.e., anti-CD3 ε nanobody) of the present invention can be conjugated with a second antibody to form a bispecific T-cell engager (BiTE), triple specific T-cell engager (TriTE), bispecific killer cell engager (BiKE), triple specific killer cell engager (TriKE), or any bispecific antibody.

In summary, the anti-T-cell nanobody (i.e., anti-CD3 ε nanobody) of the present invention can promote T cell proliferation and activation by T cell (i.e., peripheral blood mononuclear cell (PBMC)) proliferation and activation assay, enhances CD3 positive T cell proliferation in PBMCs, enhances CD3 positive T cell proliferation in γδ T (GDT) cells, could recognize CD3 ε protein from cellular lysate of human T cells by Western blotting analysis, can be used for flow cytometry analysis to detect CD3 ε expression on cell samples by immunohistochemistry staining (IHC staining) and flow cytometric analysis, effectively binds to CD3 d CD3δ heterodimer within the $K_D$ as 0.5056 nM by surface plasmon resonance binding assay (SPR binding assay), and can be used to detect the expression of CD3 ε on cell samples by immunocytochemistry, thereby achieving the effect of treating cancer, immunoregulation and activating immune cells. In particular, compared with the conventional antibodies, which have the disadvantages of low yield and poor effect, the gene must be transfected into cells by a vector to express the antibody function, the anti-T-cell nanobody of the present invention can be prepared in vitro on a large scale, and directly administered to the individual in need for treatment. In addition, the present invention can also achieve the effect of detecting the expression level of CD3 ε.

Although the present invention has been described with reference to the preferred embodiments, it will be apparent to those skilled in the art that a variety of modifications and changes in form and detail may be made without departing from the scope of the present invention defined by the appended claims.

What is claimed is:

1. An anti-T-cell nanobody that specifically binds to a CD3ε, comprising the amino acid sequence of SEQ ID NO: 1, SEQ ID NO:2, and SEQ ID NO:3, wherein the amino acid sequence of SEQ ID NO:1 is complementarity determining region 1 (CDR1), the amino acid sequence of SEQ ID NO:2 is CDR2, and the amino acid sequence of SEQ ID NO:3 is CDR3; and wherein the anti-T-cell nanobody is produced and purified from *Escherichia coli* (*E. coli*) strain HB2151.

2. The anti-T-cell nanobody according to claim 1, wherein the amino acid sequence is an amino acid sequence of a heavy chain variable domain (VHH) of the anti-T-cell nanobody.

3. The anti-T-cell nanobody according to claim 1, which is conjugated with a second antibody to form a bispecific T-cell engager (BiTE), triple specific T-cell engager (TriTE), bispecific killer cell enager (BiKE), triple specific killer cell engager (TriKE), or any bispecific antibody.

4. The anti-T-cell nanobody according to claim 3, which activates and/or aggregates CD3ε-positive cells.

5. A pharmaceutical composition, comprising the anti-T-cell nanobody according to claim 1 and a pharmaceutically acceptable carrier.

6. The pharmaceutical composition according to claim 5, wherein the amino acid sequence is an amino acid sequence of a heavy chain variable domain (VHH) of the anti-T-cell nanobody.

7. The pharmaceutical composition according to claim 6, wherein the anti-T-cell nanobody further comprises a fragment crystallizable region (Fc region).

8. The pharmaceutical composition according to claim 5, wherein the anti-T-cell nanobody is conjugated with a second antibody to form a bispecific T-cell engager (BiTE), triple specific T-cell engager (TriTE), bispecific killer cell enager (BiKE), triple specific killer cell engager (TriKE), or any bispecific antibody.

9. The pharmaceutical composition according to claim 8, wherein the anti-T-cell nanobody activates and/or aggregates CD3ε-positive cells.

* * * * *